United States Patent [19]

Sassenfeld

[11] Patent Number: 5,055,555

[45] Date of Patent: Oct. 8, 1991

[54] PURIFICATION OF G-CSF

[76] Inventor: Helmut Sassenfeld, 4098 Mattson Pl. NE., Bainbridge Island, Wash. 98110

[21] Appl. No.: 293,907

[22] Filed: Jan. 5, 1989

[51] Int. Cl.$^5$ .......................... C07K 3/24; C07K 3/28
[52] U.S. Cl. .................................. 530/351; 530/395; 530/412; 530/414; 530/413; 530/415; 530/416; 530/417; 530/418; 530/419; 530/420; 530/820; 530/827; 435/69.5; 435/70.1; 435/70.3
[58] Field of Search ................ 530/351, 395, 412–420; 435/69.5, 70.1, 70.3

[56] References Cited

U.S. PATENT DOCUMENTS 4,785,079  11/1988  Gospodarowicz ................. 530/399

FOREIGN PATENT DOCUMENTS 220520  5/1987  European Pat. Off. .

OTHER PUBLICATIONS

Welte et al., *PNAS*, 82, 1985, pp. 1526–1530.
Pharmacia Bulletin, #50-01-339, 1986, pp. 1–7.
Nicola et al., *Nature,* 314, 4/85, pp. 625–628.
Nicola et al., *Methods of Enzymology,* 116, 1985, pp. 600–619.
Neumeier et al., *Hoppe-Seyler's Z. Physiol. Chem.,* 1982, pp. 1493–1500.
Robert K. Scopes, *Protein Purification: Principles and Practice,* New York: Springer-Verlag, 1982, pp. 39–66.
White, Handler and Smith, *Principles of Biochemistry,* pp. 122–125.
Watson et al., "Purification of Homogeneity of a Human Hematopoietic Growth Factor that Stimulates the Growth of a Murine Interleukin 3–Dependent Cell Line", *J. Immunol.,* 137:854–857, (1986).
Nomura et al., "Purification and Characterization of Human Granulocyte Colony–Stimulating Factor (G–CSF)", *EMBO J.,* 5:871–876, (1986).

*Primary Examiner*—Garnette D. Draper
*Attorney, Agent, or Firm*—Christopher L. Wight

[57] ABSTRACT

A process for purifying human G-CSF from an aqueous solution including the step of adding NaCl to the solution to selectively precipitate the human G-CSF.

20 Claims, 3 Drawing Sheets

```
N   CAG CTG CTG CTG TGC CAC AGT GCA CTC TGG ACA GTG CAG GAA GCG
S                                   G   GTA CCT TTG GAT AAA AGG
                                        Val Pro Leu Asp Lys Arg

N   ACC CCC CTG GGC CCT GCC AGC TCC CTG CCC CAG AGC TTC CTG CTC   45
S   ACT CCT CTG GGC CCT GCT TCT TCT CTG CCT CAA TCT TTT CTG CTC   45
    Thr Pro Leu Gly Pro Ala Ser Ser Leu Pro Gln Ser Phe Leu Leu   15

N   AAG TGC TTA GAG CAA GTG AGG AAG ATC CAG GGC GAT GGC GCA GCG   90
S   AAA AGT CTA GAA CAA GTT AAA AAA ATC CAG GGC GAT GGT GCA GCT   90
    Lys Ser Leu Glu Gln Val Lys Lys Ile Gln Gly Asp Gly Ala Ala   30

N   CTC CAG GAG AAG CTG TGT GCC ACC TAC AAG CTG TGC CAC CCC GAG   135
S   CTT CAA GAA AAA CTG TGT GCT ACT TAT AAG CTT TGT CAT CCC GAG   135
    Leu Gln Glu Lys Leu Cys Ala Thr Tyr Lys Leu Cys His Pro Glu   45

GAG CTG GTG CTG CTC GGA CAC TCT CTG GGC ATC CCC TGG GCT CCC   180
    Glu Leu Val Leu Leu Gly His Ser Leu Gly Ile Pro Trp Ala Pro   60

CTG AGC AGC TGC CCC AGC CAG GCC CTG CAG CTG GCA GGC TGC TTG   225
    Leu Ser Ser Cys Pro Ser Gln Ala Leu Gln Leu Ala Gly Cys Leu   75

AGC CAA CTC CAT AGC GGC CTT TTC CTC TAC CAG GGG CTC CTG CAG   270
    Ser Gln Leu His Ser Gly Leu Phe Leu Tyr Gln Gly Leu Leu Gln   90

GCC CTG GAA GGG ATC TCC CCC GAG TTG GGT CCC ACC TTG GAC ACA   315
    Ala Leu Glu Gly Ile Ser Pro Glu Leu Gly Pro Thr Leu Asp Thr   105

CTG CAG CTG GAC GTC GCC GAC TTT GCC ACC ACC ATC TGG CAG CAG   360
    Leu Gln Leu Asp Val Ala Asp Phe Ala Thr Thr Ile Trp Gln Gln   120

ATG GAA GAA CTG GGA ATG GCC CCT GCC CTG CAG CCC ACC CAG GGT   405
    Met Glu Glu Leu Gly Met Ala Pro Ala Leu Gln Pro Thr Gln Gly   135

GCC ATG CCG GCC TTC GCC TCT GCT TTC CAG CGC CGG GCA GGA GGG   450
    Ala Met Pro Ala Phe Ala Ser Ala Phe Gln Arg Arg Ala Gly Gly   150

GTC CTG GTT GCC TCC CAT CTG CAG AGC TTC CTG GAG GTG TCG TAC   495
    Val Leu Val Ala Ser His Leu Gln Ser Phe Leu Glu Val Ser Tyr   165

CGC GTT CTA CGC CAC CTT GCC CAG CCC TGA
    Arg Val Leu Arg His Leu Ala Gln Pro End                        179
```

Figure 1

PURIFICATION OF G-CSF

BACKGROUND OF THE INVENTION

The present invention relates generally to protein chemistry of granulocyte-specific colony stimulating factors (G-CSF), and more particularly to a process for purifying G-CSF by selective precipitation.

The differentiation and proliferation of mammalian hematopoietic cells is regulated by secreted glycoproteins collectively referred to as colony stimulating factors (CSFs). Among these colony stimulating factors are G-CSFs, which induce differentiation and expansion of granulocyte-committed progenitor cells from multipotent hematopoietic stem cells. When administered to mammals, G-CSFs promote a dramatic increase in circulating granulocyte populations. Both murine and human G-CSFs have been isolated and partially characterized.

Due to potential clinical utility as a stimulator of granulocytic cell precursors, there is considerable interest in G-CSF. Therapeutic compositions with G-CSF activity could be employed to potentiate immune responsiveness to infectious pathogens, or to assist in reconstituting normal blood cell populations following radiation or chemotherapy-induced hematopoietic cell suppression. G-CSF may also find application in the treatment of certain leukemias, due to its ability to cause differentiation of certain neoplastic cells of hematopoietic lineage.

In order to fully characterize the biological activities of G-CSFs, methods have been developed to obtain protein from culture supernatants of cells known to constitutively produce G-CSF. For example, Watson et al. (*J. Immunol.* 137:854, 1986) reported a procedure for purifying human G-CSF produced from a 5637 bladder carcinoma. Twenty liters of 5637-conditioned medium was concentrated by 80% ammonium sulfate precipitation, and the precipitate dialyzed against phosphate-buffered saline (PBS) and fractionated on a gel filtration column at 4° C. Active fractions containing protein were pooled and subjected to three sequential reversed-phase high performance liquid chromatography (HPLC) steps. Nomura et al. (*EMBO J.* 5:871, 1986) reported a method for purifying human G-CSF produced from a human oral cavity carcinoma cell line (CHU-2), known to constitutively produce G-CSF. Serum-free CHU-2 conditioned medium was concentrated to 5 ml by ultrafiltration, which was further concentrated by applying to an Ultrogel AcA-54 gel filtration column and eluting to obtain two active fractions. Half of one fraction (containing 28 mg protein) was subjected to reversed-phase HPLC and gel-permeation HPLC to yield 140 μg protein.

Recombinant human G-CSF (rhG-CSF) has also been produced by expressing a rhG-CSF gene using an expression vector promoting secretory expression of G-CSF from transformed host cells, thus enabling production of larger quantities of hG-CSF. Although hG-CSF can be expressed in high levels in recombinant hosts, the resulting recombinant protein must be purified to homogeneity to enable clinical use. For example, Nagata et al. (*Nature* 319:415, 1986 and *EMBO J.* 5:575, 1986) reported the isolation of two cDNAs from the CHU-2 cell line which encode G-CSF protein. European Patent Application Serial Nos. 0 215 126 to Ono et al. and 0 220 520 to Yamazaki et al. disclose additional details concerning the cloning and expression of hG-CSF. Ono et al. specifically disclosed expression of CHU-2-derived G-CSF in *E. coli*. Recombinant hG-CSF was reported to have been purified by first lysing transformants to obtain cell supernatants. The supernatants were concentrated by gel filtration on an Ultrogel AcA-54 column, further concentrated with an ultrafiltration apparatus, and purified by two sequential purifications by adsorption on a reversed-phase C18 column. rhG-CSF was purified from the resulting fractions by HPLC based on molecular size and by SDS-polyacrylamide gel electrophoresis.

Copending U.S. patent application Ser. No. 7/029,742 describes recombinant hG-CSF analog proteins produced by DNA having alterations which enhance expression of rhG-CSF in yeast systems. These rhG-CSF proteins were initially purified from yeast supernatants by the multiple step methods of Watson et al. (discussed above). Significant yield losses were realized in the HPLC steps, however, because G-CSF adheres to the surfaces of glassware used in the purification process.

In an effort to overcome the aforementioned problems associated with multiple step purification methods, alternative methods of purification have been attempted, for example, precipitation of hG-CSF by addition of ammonium sulfate salt. Although hG-CSF does precipitate from aqueous solutions upon addition of ammonium sulfate salt, other proteins precipitate simultaneously. Ammonium sulfate salt does not therefore selectively purify hG-CSF.

The various purification methods described above each require multiple steps in order to achieve acceptable levels of purity. On a commercial scale, combining various steps is both impractical and uneconomical because each purification step not only adds to the cost of the final product but also causes successive yield losses of hG-CSF protein. Yield losses of hG-CSF are also caused by the tendency of G-CSF protein to adhere to the surfaces of glassware used in each step of the purification process. Thus, in order to purify large quantities of rhG-CSF economically, highly selective and simplified methods requiring fewer steps and providing higher yields of active protein are desirable.

SUMMARY OF THE INVENTION

The present invention provides a highly selective and simplified process for purifying recombinant human G-CSF (rhG-CSF) from aqueous solutions by salt precipitation. This process comprises the step of adding NaCl to an aqueous solution containing hG-CSF, thereby selectively precipitating hG-CSF. In a preferred embodiment of this invention, this process is carried out at temperatures ranging from 20°-25° C., enabling purification at ambient temperatures.

In another preferred embodiment of this invention, hG-CSF in an aqueous solution is first concentrated to greater than about 2 mg/ml by, for example, any known method of selective purification, including adsorption of the protein to a solid phase by column chromatography or batch adsorption. hG-CSF is then purified from this concentrate by adding NaCl to selectively precipitate hG-CSF.

BRIEF DESCRIPTION OF THE DRAWINGS

FIG. 1 is a comparison of native and synthetic hG-CSF sequences. The cDNA sequence of native hG-CSF is shown above the cDNA and amino acid sequences of synthetic hG-CSF[Ser$^{17}$Lys$^{22}$]. Amino acid changes in the synthetic sequences are underlined. The synthetic hG-CSF[Ser$^{17}$Lys$^{22}$] sequence includes nucleotides encoding the 6 amino acid yeast α-factor leader sequence.

DETAILED DESCRIPTION OF THE INVENTION

Figure 2:
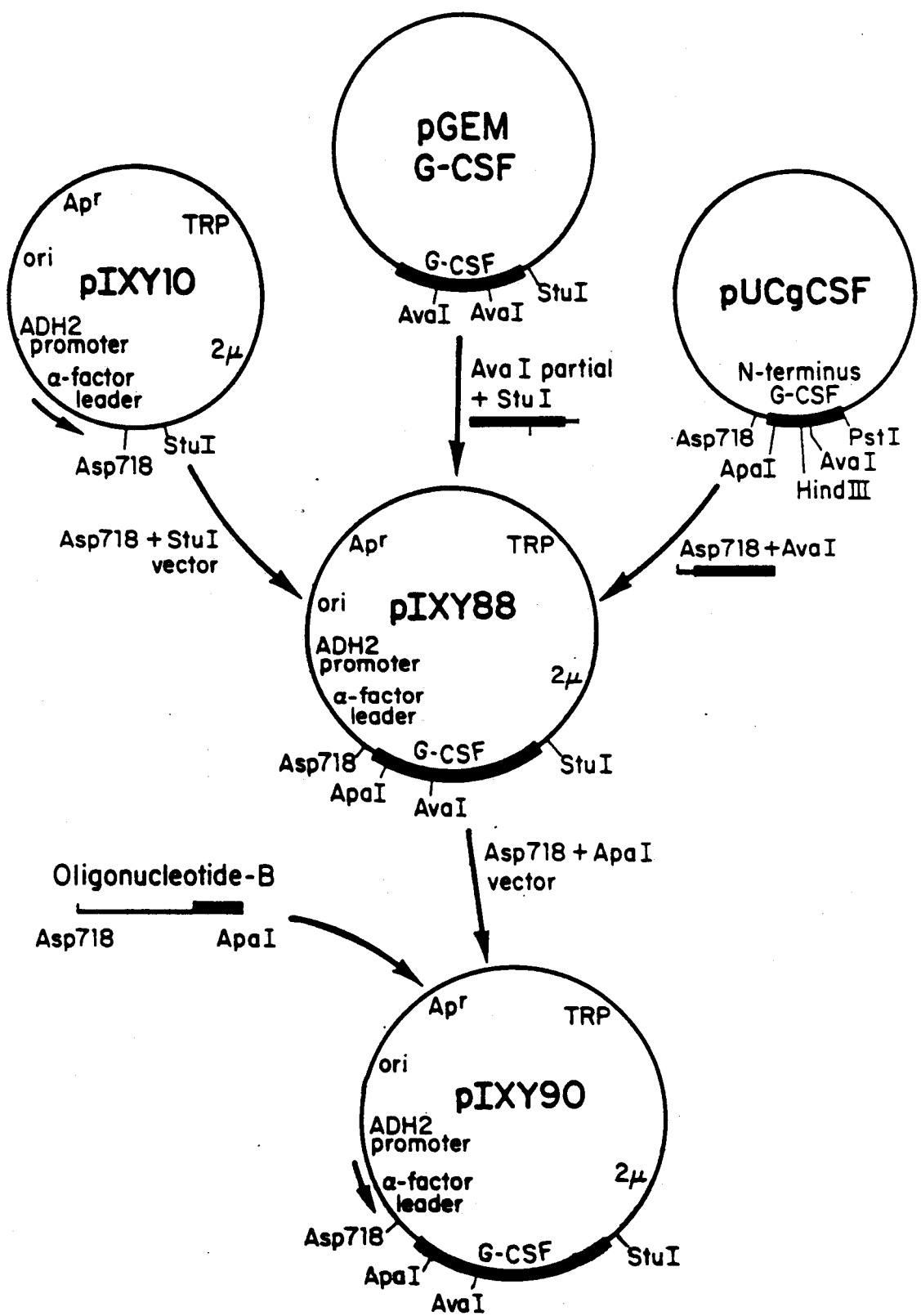
FIG. 2 is a restriction map illustrating construction of the yeast expression vector pIXY90 which directs the expression and secretion of hG-CSF and which contains an identification peptide to facilitate detection and isolation of recombinant protein with an antibody specific to the identification peptide.

As used herein, "G-CSF" or "hG-CSF" refers to a protein having substantial amino acid sequence identity with native human G-CSF, the sequence of which is disclosed in European Patent Application No. 0 220 520 to Ono et al. Native hG-CSF is a human endogenous secretory protein which selectively induces the development of granulocyte-committed progenitors from multipotent hematopoietic cells. Analog proteins are disclosed in copending U.S. patent application Ser. Nos. 6/931,458 and 7/029,742. The process of the present invention can be applied to purify both native and recombinant proteins, as well as analog G-CSF proteins, provided such analogs retain the purification characteristics of G-CSF proteins.

The term "precipitate" means an aggregate of protein molecules large enough to be visible to the naked eye and to be collected by centrifugation at about 10,000 g.

Preferably, hG-CSF is produced by recombinant microbial (e.g., bacterial or fungal) expression systems. This requires that DNA containing the hG-CSF gene be isolated and spliced into a suitable expression vector, and the vector used to transform an appropriate host strain. The host strain is then grown in culture under conditions promoting expression of the DNA to provide the desired protein. Recombinant hG-CSF can be expressed in mammalian cells, yeast, bacteria, or other cells under the control of appropriate promoters. Cell-free translation systems could also be employed to produce rhG-CSF using RNAs derived from appropriate hG-CSF DNA constructs. Appropriate cloning and expression vectors for use with bacterial, fungal, yeast, and mammalian cellular hosts are described by Pouwels et al. (*Cloning Vectors: A Laboratory Manual*, Elsevier, N.Y., 1985), the relevant portion of which are hereby incorporated by reference. European Patent Application No. 220,520 and PCT Patent Application Nos. WO 88/01297 and WO 87/01132 disclose suitable methods for expressing rhG-CSF.

Source of rhG-CSF

Exemplary methods for producing analog rhG-CSF proteins are disclosed in U.S. patent application Ser. Nos. 6/931,458 and 7/029,742, both of which are incorporated herein by reference. Briefly, a DNA segment encoding native human G-CSF is isolated from a cDNA library prepared by reverse transcription of polyadenylated RNA isolated from a human bladder carcinoma cell line, HBT 5637 (ATCC HBT-9). Synthetic oligonucleotide probes having sequence homology to N-terminal, C-terminal, and 3' non-coding regions of the native human mRNA sequence are employed to screen the library by conventional DNA hybridization techniques. DNA is isolated from those clones which hybridize to the probes and analyzed by restriction endonuclease cleavage, agarose gel electrophoresis, and additional hybridization experiments ("Southern blots") involving the electrophoresed fragments. After isolating a single clone which hybridizes to each of the probes, the hybridizing segment bearing the hG-CSF gene is then subcloned and sequenced by conventional techniques. A part of this fragment, encoding amino acids 43–174 of mature hG-CSF, is identified and cleaved from the remainder of the fragment with a particular restriction endonuclease. This DNA segment is ligated to a synthetic N-terminal sequence comprising a 3-codon deletion and added internal restriction sites. The preferred form of hG-CSF used in the present invention is a construct that is altered by site-specific mutagenesis procedures to provide mutant analog sequences in which the codon specifying Arg$^{22}$ is replaced by a codon specifying Lys, and in which the codon specifying Cys$^{17}$ is replaced by a codon specifying Ser. These mutations are employed to inactivate KEX2 protease processing sites and to alter cysteine content for high yield expression relative to the native protein. Other changes in the native sequence were also made to facilitate cloning and expression of this analog form. The nucleotide and amino acid sequences of native hG-CSF and this analog form (referred to herein as "hG-CSF[Ser$^{17}$Lys$^{22}$]") are compared in FIG. 1.

Protein Expression in Recombinant Microbial Systems

Yeast systems are preferred for the expression of rhG-CSF, and typically employ Saccharomyces species such as *S. cerevisiae*. Yeast of other genera, for example, Pichia or Kluyveromyces, have also been employed as production strains for recombinant proteins. In such systems, the DNA sequences encoding mutant or native hG-CSF are inserted into a yeast expression vector under control of a particular promoter. The vector is used to transform an appropriate yeast expression strain, which is grown in culture under conditions promoting derepression of the yeast promoter. The resulting yeast-conditioned culture supernatant is assayed to confirm enhanced expression of the analog proteins and purified to produce homogeneous rhG-CSF.

Yeast or bacterial systems can be employed for expression of recombinant analog proteins, for example, the rhG-CSF[Ser$^{17}$Lys22] mutein. An exemplary yeast expression vector is pIXY10 (shown in FIG. 2), which contains DNA sequences from pBR322 for selection and replication in *E. coli* (Ap$^r$ gene and origin of replication) and yeast DNA sequences including a glucose-repressible alcohol dehydrogenase 2 (ADH2) promoter. The ADH2 promoter has been described by Russell et al. (*J. Biol. Chem.* 258:2674, 1982) and Beier et al. (*Nature* 300:724, 1982). Plasmid pIXY10 also includes a Trp1 gene as a selectable marker and the yeast 2μ origin of replication. Adjacent to the promoter is the yeast α-factor leader sequence enabling secretion of heterologous proteins from a yeast host. The α-factor leader sequence is modified to contain, near its 3' end, and Asp718 (KpnI and Asp718 are isoschisomers) restriction site to facilitate fusion of this sequence to foreign genes, and the DYKDDDDK sequence described by Hopp et al. (*Bio/Technology* 6:1204, 1988). To allow efficient processing of secreted protein, as described by Brake et al. (*Proc. Natl. Acad. Sci. USA* 81:4642, 1984), a sequence coding for the Glu-Ala-Glu-Ala amino acids was omitted.

The choice of appropriate yeast strains for transformation is determined by the nature of the selectable markers and other features of the vector. Appropriate *S. cerevisiae* strains for transformation by pIXY10 or various constructions derived from this vector, include strains X2181-1B, available from the Yeast Genetic Stock Center, Department of Biophysics and Medical Physics, University of California, Berkeley, CA 94702, USA, having the genotype α trp1 gal1 ade1 his2; J17 (ATCC 52683; α his2 ade1 trp1 met14 ura3); and IL166-5B (ATCC 46183; α his1 trp1). A particularly preferred expression strain, XV2181, is a diploid formed by mating two haploid strains, X2181-1B, available from the Yeast Genetic Stock Center, Berkeley, CA, USA; and XV617-1-3B, available from the Department of Genetics, University of Washington, Seattle, WA 98105, USA, or Immunex Corporation, 51 University Street, Seattle, WA 98101, USA. A suitable transformation protocol is that described by Hinnen et al. (*Proc. Natl. Acad. Sci. USA* 75:1929, 1978), selecting for Trp+ transformants in a selective medium consisting of 0.67% yeast nitrogen base, 0.5% casamino acids, 2% glucose, 10 μg/ml adenine and 20 μg/ml uracil.

Host strains comprising pIXY10 or other constructions comprising the ADH2 promoter in operative association with DNA sequences encoding rhG-CSF proteins are grown for expression of rhG-CSF protein in a rich medium consisting of 1% yeast extract, 2% peptone, and 1% glucose supplemented with 80 μg/ml adenine and 80 μg/ml uracil. Derepression of the ADH2 promoter occurs upon exhaustion of medium glucose. The culture supernatants produced by the host strain contain the analog protein which is to be purified.

Purification of rhG-CSF from the culture supernatants produced by host strains first requires that the soluble and particulate fractions of the cell culture be separated. Separation of the soluble fractions from the particulate fraction is accomplished by centrifugation, filtration or other well known methods. In the preferred embodiment of the present invention, supernatants produced by a transformed yeast strain grown under conditions promoting derepression of the ADH2 promoter are filtered through a 0.45 micron filter and collected. The collected filtrate containing the rhG-CSF is then further purified to obtain homogeneous rhG-CSF.

In one preferred aspect of the present invention, hG-CSF in the crude yeast broth is concentrated to preferably greater than about 2 mg/ml by any known method of selective purification, such as, for example, ultrapurification or selective adsorption of the protein to a solid phase by column chromatography or batch adsorption. Such methods generally give the greatest increase in protein purity and specific activity. Preferably, hG-CSF is concentrated by binding hG-CSF to cation exchange media, such as S-Sepharose (Pharmacia), and subsequently displacing the hG-CSF from the column with a counterion. Other cation exchangers could also be employed.

Exemplary cation exchange media include various insoluble matrices, including cellulose-based, dextran-based, agarose-based, or synthetic polymer-based matrices comprising pendant sulfonate, sulfopropyl, or carboxymethyl functional groups. Of these, non-rigid agarose-based exchangers having sulfonate groups (e.g., S-Sepharose, Mono-S, Pharmacia) are preferred.

Solutions containing rhG-CSF are applied to cation exchange media under acid conditions, for example pH 3.0 to pH 5.0, and eluted from the media at weakly acid to weakly basic pH, for example from pH 4.0 to pH 8.0. For example, hG-CSF can be eluted from the cation exchange medium at slightly acid conditions, using an increasing gradient of NaCl or other salt, e.g., 0-1M NaCl, in 50 mM sodium acetate, pH 4.7. Alternatively, hG-CSF can be eluted from the cation exchange medium at slightly basic conditions, using multiple washes of 100 mM Tris, pH 8.0. The peak fractions containing hG-CSF are then purified by precipitation at high salt concentration as described below.

Addition of NaCl to the aqueous solution containing rhG-CSF selectively precipitates hG-CSF. However, the solubility of cytokine proteins is known to vary according to salt concentration, temperature, and pH. hG-CSF is soluble in physiological salt conditions (an ionic strength generally around 0.15–0.2M), and neutral pH.

In accordance with one aspect of the present invention, hG-CSF is precipitated at a NaCl concentration ranging from about about 2.0M to about 5.0M. These concentrations are based on solution temperatures of about 20° C. Salt concentrations less than about 2.0M have been found to precipitate protein in only small quantities. Salt concentrations greater than about 5.0M, on the other hand, are undesirable because NaCl approaches saturation and the undissolved NaCl interferes with protein precipitation and separation. Because the saturation point of NaCl is temperature-dependent, hG-CSF can be precipitated using salt concentrations higher than about 5.0M, provided temperatures higher than about 20° C. are used. However, excessive temperatures will denature the protein by disrupting hydrogen bonds holding together the secondary structure of the protein or by cleaving N-glycosidic and phosphate ester bonds. In order of increasing preference, the NaCl concentration ranges employed to precipitate rhG-CSF by the process of the present invention are about 2.0–4.0M and about 2.25–3.5M. The most preferred NaCl concentration range is about 2.5–3.0M.

Temperature also has a significant effect on the solubility of proteins. Lower temperatures improve the stability of the protein and decrease its solubility, while higher temperatures increase its solubility. Accordingly, ammonium sulfate precipitation of proteins is typically carried out at temperatures near freezing (from about 0°–4° C.). Despite the fact that it is known that higher temperatures increase the solubility of proteins, the method of purifying hG-CSF disclosed herein can be carried out at temperatures well above freezing and still provide high yields suitable for commercial scale purification of hG-CSF without corresponding loss of biological activity. As a result, the need to operate at energy-consuming low temperature conditions is eliminated. In accordance with one preferred aspect of the present invention, G-CSF is purified at room temperature, generally from about 15°–25° C.

The solubility of proteins is also markedly influenced by pH, as might be expected from their amphoteric behavior. At NaCl concentrations of between about 2.0M and 4.0M, G-CSF precipitates effectively between about pH 3–7. As the pH approaches 8, G-CSF precipitation decreases because G-CSF denatures as a result of disulfide bond shuffling. At pH values lower than about 3, proteins become deamidated, for example, causing asparagine and glutamine to lose an amide group to become respectively aspartic and glutamic acid. In order of increasing preference, the pH ranges at which hG-CSF is effectively precipitated by the process of the present invention are about pH 4-7 and pH 4.5-5.0. The most preferred pH is about pH 4.7.

It has also been observed that the degree of precipitation upon addition of NaCl varies according to the concentration of G-CSF present in the solution. Addition of NaCl to crude yeast supernatants (containing 5 µg G-CSF/ml) not only gives low yields of precipitate, but the precipitates are impure, containing other proteins in addition to G-CSF. Solutions containing 1 mg G-CSF/ml, on the other hand, give yields of about 50% G-CSF. Solutions containing 2 mg G-CSF/ml give yields of about 90%, while solutions containing 5 mg G-CSF/ml give yields of 100% (i.e., supernatants show no detectable levels G-CSF). In accordance with a preferred aspect of the present invention, hG-CSF is purified from an aqueous solution containing greater than about 2 mg G-CSF/ml, and more preferably greater than about 5 mg G-CSF/ml.

Cloning and Expression of rhG-CSF cDNA

The recombinant hG-CSF[$Ser^{17}Lys^{22}$] used in Examples 1-5 was prepared as follows.

A synthetic oligonucleotide complementary to bases 764 to 784 of the published sequence for human G-CSF (Nagata et al., *Nature* 319:415, 1986) was constructed by the standard automated triester method substantially similar to that disclosed by Sood et al. (*Nucl. Acids Res.* 4:2557, 1977) and Hirose et al. (*Tet. Lett.* 28:2449, 1978). Following synthesis, the oligonucleotide was deblocked and purified by preparative gel electrophoresis. The oligonucleotide was terminally radiolabeled using $^{32}$P-ATP and T4 polynucleotide kinase and used as a hybridization probe to screen $1.5 \times 10^5$ recombinant plaques by standard methods (Maniatis et al., 1985, supra).

A cDNA library was constructed by reverse transcription of polyadenylated mRNA isolated from total RNA extracted from a human bladder carcinoma cell line, HBT5637 (ATCC HBT9). Cells were seeded in 175 cm$^2$ flasks at $2 \times 10^4$ cells/cm$^2$, and cultured in 75-100 ml of RPMI 1640 supplemented with 5% fetal calf serum, 300 µg/ml glutamine, 50 units/ml penicillin, 50 µg/ml streptomycin, and 50 µg/ml gentamycin. Cells were harvested at a density of approximately $6 \times 10^4$ cells/cm$^2$. RNA was extracted from cell supernatants in guanidinium thiocyanate and purified by differential precipitation in ethanol (March et al., *Nature* 315:641, 1985). Polyadenylated RNA was prepared by oligo-dT cellulose chromatography (Maniatis et al., *Molecular Cloning: A Laboratory Manual*, Cold Spring Harbor, 1982). This polyadenylated RNA was then reverse transcribed. The resulting cDNA was rendered double stranded using DNA polymerase I, blunt-ended with T4 DNA polymerase, methylated with EcoRI methylase to protect EcoRI cleavage sites with the cDNA, and ligated to EcoRI linkers, essentially as described by Gubler and Hoffman (*Gene* 25:263, 1983). λgt10 arms were ligated to the cDNA, and the unit was packaged into lambda phage extracts (Strategene, San Diego, CA) according to the manufacturer's instructions to generate a library of recombinants.

The recombinants were plated on *E. coli* strain C600hfl (Huynh et al., *DNA Cloning*, Glover, ed., IRL Press, Ltd., pp. 49-78, 1985) and screened by standard plaque hybridization techniques with the labeled oligonucleotide probes. Thirty-eight positive plaques were purified and re-probed with two additional oligonucleotides complementary to bases 104 to 124 and 227 to 247 of the human G-CSF sequence (Nagata et al., 1986, supra). Two clones hybridized to both oligonucleotides, and contained cDNA inserts of approximately 1600 bp. The cDNA insert from one clone, λgt10:G-CSF, was subcloned into a derivative of pEMBL18 (Dente et al., *Nucl. Acids Res.* 11:1645, 1983) called pGEMBL18, in which the promoters for SP6 and T7 polymerases flank the multiple cloning sites. Its nucleotide sequence was determined by the chain termination method as described by Sanger et al. (*Proc. Natl. Acad. Sci. U.S.A.* 74:5463, 1977). Specifically, an EcoRI digest of λgt10:G-CSF yielded a 1560 bp fragment which was subcloned into the EcoRI site of pGEMBL18. The insert of pGEMBL:G-CSF was sequenced using a universal primer that binds adjacent to the multiple cloning site of pGEMBL18.

The sequence of the EcoRI insert of pGEMBL:G-CSF begins 44 bp upstream of the published sequence. In addition there is a 9 bp deletion (nucleotides 227 to 235 of the published sequence). The sequence includes the entire coding region of native hG-CSF (as set forth in FIG. 1) with an additional 75 bp of 5' non-coding sequence and 874 bp of 3' non-coding sequence. DNA from pGEMBL:G-CSF was used as the starting point for further manipulations.

The yeast expression vector pIXY10 (FIG. 2) includes DNA sequences from the following sources:

1. From the *E. coli* vector pBR322, the large SphI (nucleotide 562) to EcoRI (nucleotide 4361) restriction fragment which includes the origin of replication and the ampicillin-resistance marker for selection in *E. coli*.

2. From the yeast *S. cerevisiae*, DNA fragments include the TRP-1 gene as a selectable marker in yeast, derived from plasmid YRP7 (Struhl et al., *Proc. Natl. Acad. Sci. USA* 76:1035, 1979); the yeast 2µ origin of replication derived from plasmid YEP13 (Broach, *Methods Enzymol.* 101:307, 1983); the *S. cerevisiae* ADH2 promoter, obtained from the Washington Research Foundation and described by Russell et al. (*J. Biol. Chem.* 258:2674, 1983); and the 85-amino acid signal peptide derived from the gene encoding the secreted peptide α-factor. An Asp718 restriction site was introduced at nucleotide 237 in the α-factor signal peptide to facilitate its fusion to heterologous genes. The T residue at nucleotide 241 was changed to a C residue by oligonucleotide-directed in vitro mutagenesis as described by Craik (*BioTechniques*, p. 12, 1985).

3. A 215-bp fragment of DNA from the 3' non-coding region of the human Interleukin-2 (IL-2) cDNA (nucleotides 543-753), as described by Taniguchi et al. (*Nature* 302:305, 1983). This irrelevant DNA fragment remains in the vector after removing the previously included IL-2 cDNA fragment at the StuI site, nucleotide 543 (Taniguchi et al., supra).

The yeast expression vector pIXY10 was digested with the restriction enzymes Asp718 which cleaves near the 3' end of the α-factor leader peptide (nucleotide 237) and StuI, which cleaves in a polylinker region of the plasmid. The large vector fragment was purified and ligated to the following DNA fragments (FIG. 2):

1. An hG-CSF fragment derived from plasmid pGEM:G-CSF comprising nucleotides from the AvaI site to the StuI site 3' to the hG-CSF cDNA in the non-coding region (nucleotides 261 to 754 of the published sequence of Nagata et al.

2. Eight synthetic oligonucleotides (four pairs of oligonucleotide A, Table 1) were made which encoded the last six amino acids of the α-factor leader sequence (from the Asp718 site) and the first 47 amino acids of mature hG-CSF (to the first AvaI restriction site). These eight oligonucleotides contained several base changes from the published sequence of Nagata et al. that do not alter the amino acid sequence of the protein but introduce several convenient restriction sites for further manipulations (ApaI, XbaI, BstXI, and HindIII). The oligonucleotide was also constructed with a PstI site at the 3' end. The oligonucleotides were initially annealed and ligated into the *E. coli* vector pUC8 by inserting them into the KpnI and PstI sites. This vector, pUCG-CSF, was digested with Asp718 and AvaI to give a 160 bp DNA fragment encoding the last six amino acids of the α-factor leader and the first 47 amino acids of mature hG-CSF.

The resulting yeast expression vector, designated pIXY88 (FIG. 2), directs the expression and secretion of native rhG-CSF. A variation of this expression vector was created, pIXY90 (FIG. 2), which contains an eight-amino acid peptide fused to the N-terminus of hG-CSF, as described by Hopp et al. (*Bio/Technology* 6:1204, 1988). This fusion to the hG-CSF protein allowed its detection with specific antibody and was used for monitoring the expression and purification of hG-CSF. This vector was created by digesting pIXY88 with the restriction enzymes Asp718, which cleaves near the 3' end of the α-factor leader peptide, and ApaI, which cleaves after nucleotide 11 of mature hG-CSF. The large vector fragment was ligated together with oligonucleotide B (Table 1) which regenerates the 3' end of the α-factor leader, encodes the eight-amino acid fusion peptide, and regenerates the 5' end of the hG-CSF cDNA.

sis by SDS-polyacrylamide gel electrophoresis (PAGE) of wild type rhG-CSF protein purified from yeast broth suggested the presence of disulfate-linked dimers of the rhG-CSF molecule. The cysteine at position 17 of mature hG-CSF was thus changed to a serine residue. The removal of this nonessential cysteine residue prevented unwanted dimerization of the protein through disulfide bond formation. Second, the arginine at amino acid position 22 of mature hG-CSF was changed to a lysine residue. The dibasic residues Lys-Arg or Arg-Lys can serve as substrates for the proteolytic enzyme which removes the α-factor leader peptide. Thus, unwanted proteolysis of a secreted protein can be obviated by changing the arginine to a lysine residue, as Lys-Lys is a much poorer substrate for the KEX2 enzyme.

The oligonucleotide-directed site-specific mutagenesis of hG-CSF was conducted by a method similar to that described by Walder and Walder (*Gene* 42:133, 1986). The yeast vector, pIXY102, was derived from pIXY90 (FIG. 3) and includes a 514-bp DNA fragment derived from the single-stranded bacteriophage f1 containing the origin of replication and intergenic region. This fragment is inserted at the NruI site in the pBR322 DNA sequences. The presence of the f1 origin of replication allows generation of single-stranded copies of the vector when transformed into appropriate (male) strains of *E. coli* and superinfected with bacteriophage f1. This capability facilitates DNA sequencing of the vector and enables in vitro mutagenesis.

Figure 3:
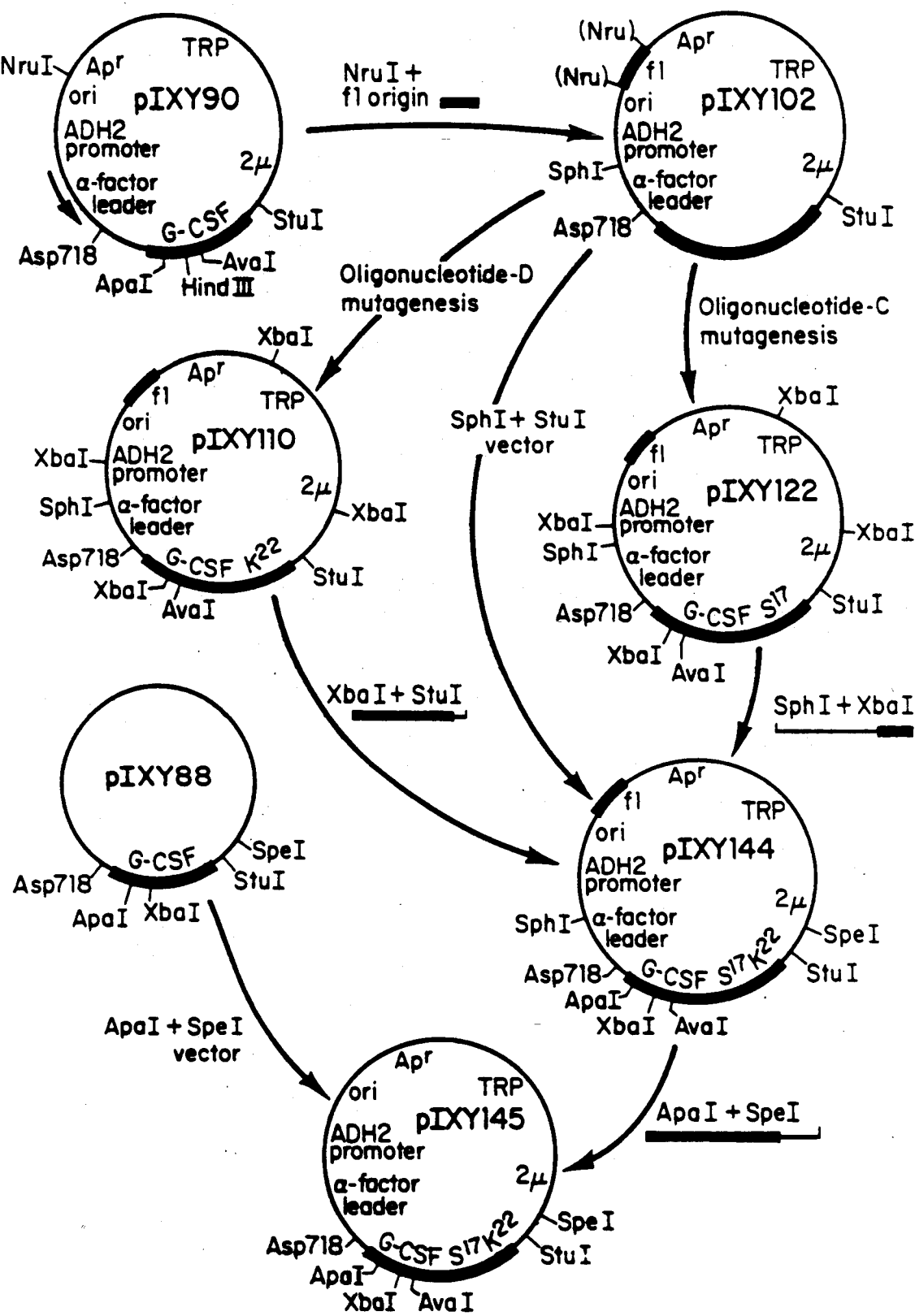
FIG. 3 is a restriction map illustrating construction of the yeast expression vector pIXY145, which directs the expression and secretion of rhG-CSF[Ser$^{17}$Lys$^{22}$].

Single-stranded DNA was generated by transforming *E. coli* strain JM107 and superinfecting with helper phage IR1. Single-stranded DNA was isolated and annealed to the mutagenic oligonucleotides C or D (Table 1). Oligonucleotide C provides a codon switch substituting Ser for Cys at position 17 of mature hG-CSF. This plasmid is designated pIXY122 (FIG. 3). Oligonucleotide D results in an Arg to Lys change at position 22 of mature hG-CSF. The plasmid containing this amino acid change is designated pIXY110 (FIG. 3). Annealing

TABLE 1

Oligonucleotide A

```
    CT TTG GAT AAA AGA ACT CCT CTG GGC CCT GCT TCT TCT CTG CCT CAA TCT TTT
CAT GGA AAC CTA TTT TCT TGA GGA GAC CCG GGA CGA AGA AGA GAC GGA GTT AGA AAA
Val Pro Leu Asp Lys Arg Thr Pro Leu Gly Pro Ala Ser Ser Leu Pro Gln Ser Phe

CTG CTC AAA TGT CTA GAA CAA GTT AGA AAA ATC CAG GGC GAT GGT GCA GCT CTT CAA
GAC GAG TTT ACA GAT CTT GTT CAA TCT TTT TAG GTC CCG CTA CCA CGT CGA GAA GTT
Leu Leu Lys Cys Leu Glu Gln Val Arg Lys Ile Gln Gly Asp Gly Ala Ala Leu Gln

GAA AAA CTG GTT TCT GAA TGT GCT ACT TAT AAG CTT TGT CAT CCC GAG CTG CAG
CTT TTT GAC CAA AGA CTT ACA CGA TGC ATA TTC GAA ACA GTA GGG CTC G
Glu Lys Leu Val Ser Glu Cys Ala Thr Tyr Lys Leu Cys His Pro Glu
```

Oligonucleotide B

```
GTA CCT TTG GAT AAA AGA GAC TAC AAG GAC GAC GAT GAC AAG ACT CCT CTG GGC C
    GA AAC CTA TTT TCT CTG ATG TTC CTG CTA CTA CTG TTC TGA GGA GAC
 Pro Leu Asp Lys Arg Asp Tyr Lys Asp Asp Asp Asp Lys Thr Pro Leu
```

Oligonucleotide C

CTG CTC AAA AGT CTA GAA CAA

Oligonucleotide D

GAA CAA GTT AAA AAA ATC CAG G

Two amino acid alterations were made in the wild type G-CSF protein to improve recombinant yeast expression and recovery of hG-CSF. First, comparison of the sequences encoding murine G-CSF and human G-CSF revealed that although both proteins contained five cysteine residues each, only four were in conserved positions between the two species. Furthermore, analyand yeast transformation conditions were done as described by Walder and Walder, supra. Yeast transformants were selected by growth on medium lacking tryptophan, pooled, and DNA extracted as described by Holm et al. (*Gene* 42:169, 1986). This DNA, containing a mixture of wild type and mutant plasmid DNA, was used to transform *E. coli* RR1 to ampicillin resistance. The resulting colonies were screened by hybridization to the radiolabeled mutagenic oligonucleotide, using standard techniques. Plasmids comprising DNA encoding hG-CSF Ser[17], or hG-CSF Lys[22] were identified by hybridization to radiolabeled oligonucleotide C and D, respectively, under stringent conditions and verified by nucleotide sequencing.

The yeast expression plasmid pIXY144 (FIG. 3) was then constructed containing the hG-CSF cDNA encoding both the Ser[17] and Lys[22] amino acid changes. The pIXY144 vector was constructed by ligating together the following three DNA fragments: (1) the SphI to StuI restriction fragment from the yeast vector pIXY102 (FIG. 3) containing a portion of the ADH2 promoter region, (2) the SphI to XbaI fragment from pIXY122 comprising the ADH2 promoter and α-factor leader and N-terminal 17 amino acids of hG-CSF (including Ser[17]) to the XbaI site in hG-CSF (FIG. 3), and (3) the XbaI to the StuI fragment from pIXY110 which encodes the C-terminal portion of hG-CSF from the XbaI site at amino acid 17 to the StuI site in the 3' noncoding region. This fragment from pIXY110 includes the Lys[22] amino acid substitution. The resulting vector is capable of expressing hG-CSF[Ser[17]Lys[22]] with the eight amino acid identification peptide fused to the N-terminus.

The final yeast expression vector (designated pIXY145) which was constructed is identical to pIXY144 in that it encodes hG-CSF[Ser[17]Lys[22]], but it does not have the 8-amino acid identification peptide fused to the N-terminus. This expression vector was made by ligating together: (1) the vector fragment from pIXY88 from the ApaI site (nucleotide 11 of mature hG-CSF, thus encoding the mature hG-CSF N-terminus) to a SpeI site which lies 3' to the cDNA insert in the yeast vector, and (2) the hG-CSF[Ser[17]Lys[22]] cDNA-containing fragment from the ApaI site (nucleotide 11 of mature G-CSF) to the SpeI site 3' to the hG-CSF cDNA in the yeast vector (FIG. 3). This vector, when present in yeast, allows glucose-regulated expression and secretion of mature hG-CSF[Ser[17]Lys[22]]. The α-factor leader is proteolytically removed after the Lys-Arg residues (amino acids 83 and 84 of the leader) by the product of the KEX2 gene (Julius et al., *Cell* 37:1075, 1984; Brake et al., *Proc. Natl. Acad. Sci. USA* 81:4642, 1984), resulting in the production of hG-CSF with the correct N-terminus.

Standard molecular biological techniques were followed as described in Maniatis et al., supra, for the restriction enzyme digestion of DNA, purification of DNA fragments by gel electrophoresis, ligation of DNA fragments, transformation into E. coli (strain RR1 was used throughout, except for generating single-stranded DNA in JM107), and analysis and verification of constructs by restriction enzyme digestion.

The host strain used for expression of rhG-CSF[Ser[17]Lys[22]], XV2181, was a diploid *S. cerevisiae* strain formed by mating the following two haploid strains: XV617-1-38 [a, His6, Leu2-1, trp1-1, Ura 3, Ste5], obtained from the University of Washington, Department of Genetics Yeast Strain Bank, Seattle, Wash., USA, and X2181-1B [α, trp1-1, gal1, ade1, his2], obtained from the Yeast Genetic Stock Center, University of California, Berkeley, Calif., USA.

The two haploid strains were mated by mixing the cells together on rich medium (per liter: 20 g peptone, 10 g yeast extract, 20 g glucose, 15 g agar). The two strains mate to form diploids with the genotype [a/α, trp1-1] and are selected for by plating on medium lacking leucine and adenine. On such medium, neither haploid strain will grow; only the diploids are viable.

The diploid host strain was further verified by its inability to grow in the absence of tryptophan (using the same selective medium containing 0.5% casamino acids, which lack tryptophan, instead of the amino acid supplements) and its ability to grow on medium lacking uracil or histidine. (Selective medium [YNB −Leu, −Ade: per liter] as described in Table 2 below lacks the amino acids of interest.)

TABLE 2

| Component | Amount | Source |
|---|---|---|
| Yeast Nitrogen Base (YNB) | 6.7 g | Difco |
| Glucose | 20.0 g | Sigma |
| Agar | 15 g | Difco |
| With the Following Supplements: | | |
| L-arginine | 14 μg/ml | Sigma |
| L-aspartic acid | 70 μg/ml | Sigma |
| L-glutamic acid | 70 μg/ml | Sigma |
| L-histidine | 14 μg/ml | Sigma |
| L-isoleucine | 56 μg/ml | Sigma |
| L-lysine | 42 μg/ml | Sigma |
| L-methionine | 14 μg/ml | Sigma |
| L-phenylalanine | 35 μg/ml | Sigma |
| L-serine | 285 μg/ml | Sigma |
| -threonine | 142 μg/ml | Sigma |
| L-tyrosine | 42 μg/ml | Sigma |
| L-tryptophan | 14 μg/ml | Sigma |
| -uracil | 14 μg/ml | Sigma |
| L-valine | 100 μg/ml | Sigma |
| L-leucine | 56 μg/ml | Sigma |

A production strain capable of synthesizing and secreting hG-CSF was made by transforming the host strain, XV2181, with the expression plasmid pIXY145. Transformation of the host strain with the expression plasmid was performed by the lithium acetate procedure described by Sherman et al. (*Laboratory Course Manual for Methods in Yeast Genetics*, Cold Spring Harbor Laboratory, p. 121, 1986), or the spheroplasting procedure described by Hinnen et al. (*Proc. Natl. Acad. Sci. USA* 75:1929, 1978) selecting for Trp+ transformants.

A single colony isolate was picked from the initial transformation plate and restreaked onto a selective plate (YNB-trp, as described above) to verify the Trp+ phenotype of the transformants. The working cell seed was stored by inoculating liquid medium (YNB-trp) with a single colony isolate from the selective plate and growing the culture at 30° C. for 18 hours until high cell density (late log phase). The culture was made 20% in sterile glycerol and 1 ml aliquots were aseptically dispensed into 1.5 ml sterile Eppendorf tubes. The aliquoted cultures were stored frozen at −70° C.

DNA from the working cell seed was isolated essentially as described by Holm et al., 1986. The DNA was transformed into *E. coli* strain RR1 or JM107 for amplification in preparation for DNA sequence analysis to verify the hG-CSF coding region. The DNA sequence of the hG-CSF coding region was determined by the methods previously described. The DNA sequence was found to be identical to that found for the cDNA isolate, with the predicted amino acid changes from Cys to Ser at position 17 and Arg to Lys at position 22.

Each of the foregoing transformants was fermented under conditions promoting derepression of the ADH2 promoter, and the fermenter contents were harvested.

The crude yeast broth containing the rhG-CSF was then filtered through a filter system equipped with a 0.45 micron filter and collected for purification as described below in Examples 1-5.

EXAMPLE 1

Purification from Crude Yeast Broth

This experiment was conducted to determine the yield of rhG-CSF that could be obtained from crude yeast broth by selective precipitation. Four 200 ml aliquots of crude yeast broth containing rhG-CSF[Ser$^1$-7Lys$^{22}$], prepared as described above, were adjusted to pH 3.0 (buffered with 20 mM glycine), pH 4.0 (buffered with 20 mM β-alanine), pH 4.7 (buffered with 20 mM sodium acetate), and pH 8.2 (no buffer) and chilled on ice to approximately 4° C. To each of these samples was added 30 g NaCl to bring each solution to a final molarity of 2.5. The salt was completely dissolved in each solution, and each solution was incubated for 30 minutes at 37° C. and centrifuged for 45 minutes at 13,000 g to obtain a small light brown precipitate. The supernatants were decanted and retained. The residual precipitates were then resuspended in 10 ml of 100 mM Tris, and adjusted to pH 7.4. SDS-PAGE analysis of the supernatants and precipitates indicated that most of the G-CSF remained in the supernatants. The light brown color of the precipitate also indicated that the precipitate contained impurities. This experiment thus indicates that G-CSF does not precipitate efficiently from crude yeast extracts at concentrations of about 5 μg/ml and at pHs ranging from 3.0 to 8.2.

EXAMPLE 2

Purification of rhG-CSF

This experiment was conducted to determine relative recovery of rhG-CSF at various NaCl concentrations and pH. Recombinant hG-CSF[Ser$^{17}$Lys$^{22}$] was produced in a yeast expression system as described above. The G-CSF in the resulting crude yeast broth was bound to S-Sepharose gel (Pharmacia) by batch adsorption. S-Sepharose gel slurry (1 volume gel:1 volume distilled water) is added to the yeast broth. The resulting yeast broth/gel suspension is adjusted to pH 3.0 by adding 2N HCl and stirred for 10 minutes, and then filtering the suspension using a sintered glass funnel to collect the gel. The gel was washed with 50 mM MES (N-morpholinoethane sulfonic acid), pH 6.0, and G-CSF was eluted with multiple washes of 100 mM Tris, pH 8.0. Thirty 10 ml aliquots of the peak pool were adjusted to salt concentrations varying from 1.5 to 4.0M, and pHs of 3.7, 4.0, 4.2 and 4.7. The pH of each aliquot was adjusted by diluting the solution from 2.5 mg G-CSF/ml to 2 mg/ml by adding 200 μl of a 1M stock of an appropriate buffer.

Solid NaCl was added to each diluted aliquot. The solution was mixed and incubated for 10 minutes before centrifuging at 10,000 g for 30 minutes at room temperature. Supernatants were removed and the precipitates resuspended to the original volume in 10 mM Tris, pH 7.4. The efficiency of the protein precipitation was measured by the Biorad or BCA protein assay (Biorad, Rockville Centre, New York, USA, and Pierce Chemical Company, Rockford, Ill., USA, respectively). The percentage recovery of rhG-CSF by NaCl salt precipitation, at various NaCl concentrations and pH, are set forth in Table 3 below. One aliquot of the diluted peak fraction was left in 100 mM Tris, pH 8.2 and precipitated as a control at 2.5M NaCl. The protein assay values were confirmed by visual inspection of silver stain PAGE on Phast Gels (Pharmacia). These experiments indicated that recovery of protein was highest at pH 4.7 and NaCl concentration from 2.5 to 2.75M.

TABLE 3

| Molarity | % Recovery of Protein pH | | | |
|---|---|---|---|---|
| | 3.7 | 4.2 | 4.7 | 8.2 |
| 1.5 | 76 | 77 | 26 | |
| 2.0 | 71 | 71 | 45 | |
| 2.25 | 71 | 68 | 39 | |
| 2.5 | 61 | 59 | 86 | 50 |
| 2.75 | 60 | 47 | 92 | |
| 3.0 | 49 | 46 | 76 | |
| 3.5 | 42 | 33 | 79 | |
| 4.0 | | | 76 | |

EXAMPLE 3

Purification of rhG-CSF

Using the methods described above in Example 2, rhG-CSF was purified by precipitation at NaCl concentrations ranging from 1.5 to 3.5M at pH 4.0, using peak pool fractions containing 8 mg/ml rhG-CSF. Percentage recovery from the starting material is set forth in Table 4 below. At NaCl concentrations of 1.5, 2.0 and 2.25M, percentage recovery was estimated based on visual inspection of Phast Gels. Yields were generally higher than those in Example 2, apparently due to the higher concentration of rhG-CSF protein in the starting material. These data demonstrate that salt precipitation is more efficient with solutions containing higher concentrations of protein.

TABLE 4

| Molarity | % Recovery of Protein at pH 4.0 |
|---|---|
| 1.5 | ≦50 |
| 2.0 | ≦50 |
| 2.25 | ≦50 |
| 2.5 | 84 |
| 2.75 | 89 |
| 3.0 | 87 |
| 3.5 | 84 |

EXAMPLE 4

The following example illustrates a large scale process for purifying rhG-CSF using the methods of the present invention. Yeast broth produced by the methods described above and containing rhG-CSF[Ser$^1$-7Lys$^{22}$] is harvested and filtered through a 0.45 micron filter into sterile vessels. The G-CSF contained in the collected yeast broth filtrate is bound to S-Sepharose gel by batch adsorption. To a volume of approximately 30 l of yeast broth, approximately 600 ml of S-Sepharose gel slurry (1 volume gel:1 volume distilled water) is added. This suspension is adjusted to pH 3.0 by adding 2N hydrochloric acid (HCl) and stirred for 10 minutes. The yeast broth/gel mixture is then filtered, using a sintered glass funnel to collect the gel.

The resulting gel (approximately 300 ml, from processing 30 L yeast broth) is washed with 3 L of 50 mM MES (N-morpholinoethane sulfonic acid), pH 6.0. The G-CSF is then eluted with four 300 ml washes of 100 mM Tris, pH 8.0. The elutions are pooled, sterile filtered, and stored at 2°-8° C.

The pooled S-Sepharose elutions are made 20 mM in glycine and adjusted to pH 3. This solution is applied at 6 ml/min to a MONO S HR 16/10 column (Pharmacia) equilibrated in 50 mM glycine, pH 3.0. All MONO S buffers are prepared using sterile water for irrigation. After application of G-CSF, the column is washed with 50 ml of 50 mM glycine pH 3.0, followed by 140 ml of 50 mM sodium acetate, pH 4.7. G-CSF is then eluted with a linear gradient (0–0.5M sodium chloride, 50 mM sodium acetate, pH 4.7) over 100 ml. Fractions containing G-CSF are pooled, sterile filtered and stored at 2°–8° C.

MONO S purified G-CSF (>5 mg/ml) is pooled and diluted with an equal volume of 5M sodium chloride, 50 mM sodium acetate, pH 4.7 (prepared with sterile water for irrigation). After 10 minutes, the preparation is centrifuged at room temperature (14,000 g, 30 minutes, 20° C.). The supernatant is removed and the white G-CSF precipitate is dissolved in 100 mM Tris, pH 7.4 (prepared with sterile water for irrigation). The solution is then dialyzed against 100 volumes of 100 mM Tris, pH 7.4, sterile filtered, and stored at 2°–8° C.

EXAMPLE 5

In the preferred method of practicing the present invention, 5 l of filtered yeast broth containing rhG-CSF[$Ser^{17}Lys^{22}$] is produced by the process described above and adjusted to pH 3.0 by adding 2N HCl. The solution is applied to an ion exchange column (22 mm diameter, adjusted to 13 cm length) (Amicon Corp., Danvers, Mass., USA), which was packed with 50 ml S Sepharose gel (Pharmacia) and preequilibrated in 20 mM glycine, pH 3.0. The column is washed with 3 volumes of 50 mM sodium acetate, pH 4.7. G-CSF is then eluted from the column with a salt gradient of 50 mM sodium acetate, pH 4.7, from 0–1M NaCl, in 25 ml fractions.

G-CSF is precipitated by adding solid NaCl to the S Sepharose peak fraction to bring the fraction to a final concentration of 2.5M. The preparation is centrifuged at room temperature (14,000 g, 30 minutes, 20° C.) to obtain a white precipitate. The supernatant is removed and the remaining white G-CSF precipitate is resuspended in approximately 1/6th the original S Sepharose peak volume (8 ml) with 10 mM Tris, pH 7.4, 4% mannitol, 1% sucrose.

We claim:
1. A method of purifying human G-CSF (hG-CSF) from an aqueous solution containing hG-CSF comprising the steps of
   (a) adding NaCl to said an aqueous solution containing greater than about 1 mg/ml hG-CSF to selectively precipitate hG-CSF; and
   (b) isolating the precipitate from the solution.
2. The method of claim 1 carried out at between about 15° C. and about 25° C.
3. The method of claim 1, wherein said aqueous solution contains G-CSF at a concentration greater than about 2 mg/ml.
4. The method of claim 3, wherein sufficient NaCl is added to bring the NaCl concentration in said solution to between about 2.0 and about 4.0M.
5. The method of claim 4, wherein the pH of said solution is from about 4 to about 7.
6. A method of purifying human G-CSF (hG-CSF) from an aqueous solution containing hG-CSF comprising the following steps:
   (a) concentrating hG-CSF in said aqueous solution to greater than about 1 mg/ml;
   (b) adding NaCl to said concentrated solution containing hG-CSF to selectively precipitate hG-CSF; and
   (c) isolating the precipitate from the solution.
7. The method of claim 6, wherein hG-CSF is concentrated by cation exchange chromatography.
8. The method of claim 7, wherein the cation exchange chromatography is carried out using a stationary phase selected from the group consisting of cellulose-based, agarose-based, dextran-based and synthetic polymer-based matrices having functional moieties selected from the group consisting of sulfonate, sulfopropyl and carboxymethyl groups, and the hG-CSF is absorbed onto said stationary phase.
9. The method of claim 7, further comprising the step of eluting the hG-CSF from the stationary phase with a NaCl salt gradient.
10. The method of claim 6, wherein the selective precipitation step is carried out at between about 15° C. and about 25° C.
11. The method of claim 6, wherein the hG-CSF is selectively precipitated by adding sufficient NaCl to bring the NaCl concentration in said solution to between about 2.0 and about 4.0M.
12. The method of claim 11, wherein the pH of said solution is from about 4 to about 7.
13. A method of purifying human G-CSF (hG-CSF) comprising the steps of:
   (a) culturing cells capable of expressing hG-CSF in an aqueous culture medium;
   (b) recovering said hG-CSF from said medium;
   (c) concentrating said hG-CSF in said medium to greater than about 1 mg/ml by adsorbing said hG-CSF to a cation exchanger;
   (d) eluting said hG-CSF from said cation exchanger;
   (e) adjusting to between about pH 4 and pH 7;
   (f) adding NaCl to said concentrated medium containing hG-CSF to thereby selectively precipitate said hG-CSF; and
   (g) isolating the precipitate from the solution.
14. The method of claim 13, wherein the cation exchanger is selected from the group consisting of cellulose-based, agarose-based, dextran-based and synthetic polymer-based matrices having functional moieties selected from the group consisting of sulfonate, sulfopropyl and carboxymethyl groups, and the hG-CSF is adsorbed onto said stationary phase.
15. The method of claim 14, wherein the hG-CSF is eluted from the cation exchanger with a NaCl salt gradient.
16. The method of claim 15, wherein hG-CSF is selectively precipitated by adding sufficient NaCl to bring the NaCl concentration to between about 2.0M and about 4.0M.
17. The method of claim 16, wherein sufficient NaCl is added to bring the NaCl concentration to between about 2.5M and about 3.0M.
18. The method of claim 14, wherein the cation exchange is selected from the group consisting of S-Sepharose and Mono-S.
19. The method of claim 13, wherein said selective precipitation step is carried out at between about 15° C. and about 25° C.
20. The method of claim 13, wherein said hG-CSF is expressed in yeast cells.

* * * * *

UNITED STATES PATENT AND TRADEMARK OFFICE
CERTIFICATE OF CORRECTION

PATENT NO. : 5,055,555

DATED : October 8, 1991

INVENTOR(S) : Helmut Sassenfeld

It is certified that error appears in the above-identified patent and that said Letters Patent is hereby corrected as shown below:

Column 15, line 65 add -- about -- before the number 7.

Signed and Sealed this

Twenty-third Day of March, 1993

Attest:

STEPHEN G. KUNIN

*Attesting Officer*     Acting Commissioner of Patents and Trademarks